United States Patent [19]
Adolf et al.

[11] Patent Number: 5,514,123
[45] Date of Patent: *May 7, 1996

[54] STERILE FORMED, FILLED AND SEALED FLEXIBLE CONTAINER

[75] Inventors: Wayne F. Adolf, Mt. Prospect; R. Hayes Helgren, Mundelein, both of Ill.; James T. Renick, Bristol, Wis.; Walter T. Szempruch, Gurnee, Ill.

[73] Assignee: Abbott Laboratories, Abbott Park, Ill.

[*] Notice: The portion of this patent shall not extend beyond the expiration date of Pat. No. 5,334,150.

[21] Appl. No.: 217,028

[22] Filed: Mar. 28, 1994

Related U.S. Application Data

[63] Continuation-in-part of Ser. No. 41,797, Apr. 1, 1993, Pat. No. 5,334,180.

[51] Int. Cl.$^6$ .................................................. A61B 19/00
[52] U.S. Cl. ........................... 604/411; 604/905; 383/67; 383/906; 222/81
[58] Field of Search ............................... 604/86–88, 408, 604/411, 905; 222/81–83, 83.5, 84–91; 383/67, 906

[56] References Cited

U.S. PATENT DOCUMENTS

| 5,048,723 | 9/1991 | Seymour | 222/81 |
| 5,222,950 | 6/1993 | Eisenberg | 604/408 |
| 5,328,664 | 7/1994 | Ponsy | 222/81 X |
| 5,334,180 | 8/1994 | Adolf et al. | 604/905 X |
| 5,356,380 | 10/1994 | Hoekwater et al. | 604/905 X |

Primary Examiner—Mary Beth Jones
Attorney, Agent, or Firm—A. Nicholas Trausch

[57] ABSTRACT

The present invention relates to a sterile form, filled and sealed flexible solution container and an attached port assembly that allows for the sterile dispensing of the solution. In particular, the present invention relates to a sterile formed, filled and sealed flexible solution container and a sterile administration port assembly which is attached without interrupting the complete sealing of the hermetically sealed fluid container and which allows for the sterile packaging, storage and delivery of a sterile medical solution without heat degradation or oxygen permeation.

10 Claims, 8 Drawing Sheets

STERILE FORMED, FILLED AND SEALED FLEXIBLE CONTAINER

This application is a continuation-in-part application of commonly assigned U.S. patent application Ser. No. 08/041,797 filed Apr. 1, 1993, entitled "Sterile Formed, Filled and Sealed Flexible Container", now U.S. Pat. No. 5,334,180. The benefit of the filing date of this prior pending patent application is hereby claimed under 35 USC 120.

FIELD OF THE INVENTION

The present invention relates to a sterile formed, filled and sealed flexible solution container with an attached administration port system and, in particular, to a sterile formed, filled and sealed flexible solution container and a sterile administration port assembly which is attached without interrupting the complete sealing of the hermetically sealed fluid container and which allows for the sterile packaging, storage and delivery of a sterile medical solution without heat degradation or oxygen permeation.

BACKGROUND OF THE INVENTION

Various foodstuffs, liquids and other degradable material can be sterilely packaged in pouch-type flexible containers made from webs of flexible film that are folded and sealed together along the unconnected peripheral sides. This type of flexible packaging is commonly referred to as form, fill and seal packages. There are a number of advantages to these pouch-type flexible containers, including weight, durability and low cost to produce. To a lesser extent, a few medical solutions have been sterilely packaged in pouch-type flexible containers by form, fill and seal packaging machines.

One disadvantage of these pouch-type flexible containers for medical solution use is that it is difficult to make a sterile connection to the flexible container for withdrawing the contents in a sterile manner. The wall material of the container is flexible and without any rigidity. Thus, it is difficult to obtain a liquid tight and leakproof connection through the flexible wall using traditional medical connectors such as needles or piercing pins.

Traditionally, it has been necessary for flexible solution containers used for parenteral solutions to include administration pods to facilitate sterile and liquid tight access to the solution. These pre-formed, administration ports are often molded from a suitable medical grade plastic material. The usual considerations for the material used for the administration ports are the ease of molding and the ability to be securely bonded to the flexible film sheets forming the container. For example, an administration port may be sealed by many known thermal bonding processes between the opposed inner layers of two flexible film sheets so as to form a flexible solution container with an administration port. Ultrasonic welding or solvent bonding may also be used to seal the boat port between the film layers.

The majority of flexible films used for flexible solution containers are monolayer PVC films. Recently, a few multiple-layer, extrusion or adhesive laminated films have been used in form, fill and seal packaging for producing flexible solution containers. The inner, solution contacting film layer must be substantially inert to the solution. Also the inner layer of the film must be readily bondable to itself when it is folded over. Furthermore, the other, i.e. outer, film layer must be bondably compatible with the plastic material used for the attachable administration port. The outer layer of the laminated film must be durable and also compatible with other materials that may contact or be attached to the outside surface. If neither the inner or outer layer has the desired solution maintaining and barrier characteristics, such as low moisture and/or oxygen permeability, additional film layers may be required between the inner and outer layers.

A primary disadvantage of known flexible solution containers assembled according to the above described inserted port construction is that the port material typically has a higher oxygen permeability than the film material; that is, the port is a "hole" in the sealed bag material. The permeability characteristic of the port material is much poorer than the similar characteristic for the laminated film used to make the flexible container. Thus, the administration port of known flexible solution containers is often the weakest part of the barrier characteristics. This factor becomes extremely important for certain medical solutions which are sensitive to oxygen or other penetrating gases, for example.

In the past, any of the above deficiencies has been overcome by overwrapping the flexible solution container and/or the administration ports, with a high permeability overwrap material. While this redundancy in packaging may provide the desired barrier characteristics, the overwrap material introduces two important disadvantages. First, there is the additional cost to fabricate and later dispose of the overwrap. Second, there is concern that extractibles from the overwrap material may migrate into the contained solution during post filling procedures, such as during a heat sterilization process or even during shelf life.

Pre-formed administration ports constitute potential places of leakage and are potential points of entry in an otherwise sealed, durable, flexible container. Moreover, the ports make it more difficult to arrange an outer protective overwrap package around the flexible container. Also the protective overwrap only initially prevents the packaged solution from losing its potency due to evaporation or diffusion. When the overwrap is removed or breached, the administration ports positioned between two layers of film is an effective breach or "hole" in the barrier characteristics of the flexible container for certain sensitive drugs.

For example, due to the sensitivity of certain solutions to oxygen, such as amino acids, it is desirable to use materials that minimize the permeation of oxygen for the flexible solution containers for the parenteral administration of these solutions. The properties of the flexible container film can be controlled easily by the choice of the film components and structure. However, the oxygen permeation properties of the port system are not as easily controlled. Thus, it is desirable to use the film and its good barrier properties as both the solution contacting surface and the pierceable diaphragm of the administration port system so that the poorer barrier properties of the port system do not reduce the higher barrier properties of the flexible container. However this consistency is not achievable in known flexible containers having preformed rigid port systems sealed between the film layers of the flexible container.

Moreover, the known flexible container and administration port systems often include an entry port in addition to the administration port. The entry ports are likewise inserted between film layers at the perimeter seal. Both ports are thus a breach or "hole" through an otherwise effective perimeter barrier. A pierceable diaphragm is provided in the administration port to prevent an outflow of solution. During packaging, the flexible container may be filled through the entry port. After filling, the entry port is sealed, but the ports, and specifically the exposed port material, is the potential weak point for compromising the barrier characteristics.

Flange ports are an alternative to inserted ports and may be advantageously sealed to a film surface. However for the majority of flexible solution containers produced by the known form, fill and seal processes, the use of flange ports does not remove the barrier deficiency. For example, a flexible parenteral solution container including a flange-sealed port assembly is disclosed in U.S. Pat. No. 4,695,337 to Christine and in U.S. Pat. No. 4,779,397 to Christine et al. A major disadvantage of the disclosed flexible solution container is that the flexible film barrier of the flexible container is purposefully breached during the assembly steps to mount and seal the administration port or fitment to the inside surface of the flexible container, as seen for example in FIGS. 4a–4d of the patents.

Thus, due to the inherent breaches or "holes" in the film barriers of known form, filled and sealed flexible solution containers in current use, parenteral solutions may be subjected to the same degradation during the shelf life of the product solution as to breaching ports such as inserted ports. While an overwrap may provide some protection for the flexible container and the port administration system from contamination or degradation during shelf life, the overwrap introduces additional concerns that are increasingly desirable to avoid.

Thus, it is desirable to utilize the unbreached and completely intact film of form, filled and sealed flexible solution containers as the primary barrier for medical solutions packaged in flexible solution containers and especially for certain oxygen or other gas sensitive parenteral solutions.

It is therefore desirable to manufacture a form, filled and sealed flexible container that provides integral barrier characteristics without any compromises in the barrier characteristics of the film material used for the flexible solution container.

It is also desirable to manufacture a form, filled and sealed flexible container that includes an attached administration port system that is accessible by a variety of piercing pins, including center point pins, beveled pins and blunt pins as well as a port system that is compatible with the various lengths and other dimensions of the most common of these administration pins.

It is also desirable to manufacture a flexible container that allows the maximum amount of solution to be readily, completely and easily delivered in a sterile manner from the container.

SUMMARY OF THE INVENTION

The present invention relates to a sterilely formed, sterilely filled, and sterilely sealed flexible solution container including a sheet of laminated flexible film folded over along a saddle line so that a portion of the inner surface of the sheet faces a second portion of the inner surface of the sheet. A continuous peripheral line of sealing contact along the perimeter of the facing portions of this sheet is provided so as to form a sealed inner chamber between the first and second facing portions of the film. An administration port including a tubular member having a first and second open end is provided for attachment to the outer surface of the flexible container. An integral circumferential flange surrounds the first open end of the tubular port and the flange is circumferentially sealed generally along the axis of an outwardly extending sump portion. The sump portion is formed in the bottom surface of the flexible film of the formed, filled and sealed chamber. The integrity of the sealed chamber is not compromised by the attached tubular port. An access fitment is provided on the second open end of the tubular port and a removable cover for closing the second open end is provided. A penetrator element is slidably contained within the tubular port and has a contained sharp end for slidably moving relative to the circumferential flange at the first open end of the tubular port member so as to pierce the diaphragm film surface and penetrate the sealed inner, fluid containing chamber. At least one fluid passageway through the penetrator element from the pierced sealed chamber to the access fitment is provided.

More specifically, the present invention relates to an administration port for use with a formed, filled and sealed, flexible solution container. The port includes a tubular body having a first and second open end. A circumferential flange surrounds the first open end of the tubular body and is circumferentially sealable to the outer surface of the flexible container. An access fitment is provided at the second open end of the tubular body. A resilient or elastomeric cover is removably attached to the access fitment to initially close the second open end of the tubular body and maintain the sterile condition of the port system until used. A piercing mechanism or penetrator is provided in the administration port to initiate fluid flow communication from the sealed flexible container to the access fitment. In a preferred embodiment, the penetrator element includes a slidably cylindrical member initially wholly contained within the tubular body. The penetrator has a sharp end for slidably moving relative to the circumferential flange so as to pierce the film forming the diaphragm to the sealed inner chamber. The penetrator includes a hollow portion opening into the sharp beveled edge at the front end. A passageway is provided through the penetrator element from the pierced surface of the sealed container to the access fitment for sterile fluid flow of the solution from the flexible container.

The present invention is also directed to a method for sterile forming, filling and sealing a continuous, longitudinal strip of flexible laminated film into a plurality of individual flexible fluid filled containers. The continuous film strip enters a sterile manufacturing core and is sterilized and dried by any suitable sterilizing process. The flat, continuous film strip is continuously indexed through the sterile core. Next a plurality of longitudinally orientated center portions are outwardly stretched to form a plurality of discrete fluid sumps. The continuous film strip is then formed into a continuous U-shaped trough having a rounded bottom surface and two inside facing surfaces. Transverse portions of the sides surfaces are sealed together and with the bottom surface forms an open pouch or pocket. The pocket is filled with a separately pre-sterilized solution and the top edge of the pouch is sealed to form a sealed, fluid filled inner chamber. As a final step, the continuous strip of containers is cut along each transverse seal so as to form individual flexible solution containers.

Other feature and advantages of the present invention will become readily apparent from the following detailed description, the accompanying drawings, and the appended claims.

DESCRIPTION OF THE PREFERRED EMBODIMENT

Referring now to FIGS. 1–2 and 3–4, a flexible solution container 10 and port assembly 12 for maintenance and delivery of a sterile medical solution is shown. The flexible container is fabricated from a sheet of flexible, multiple-layer film, such as for example an extrusion laminated film or an adhesive laminated film. The laminated film has at least a first bondable surface layer, the desired inner barrier layers, and a second bondable surface layer. The film is folded, sealed along the sides, filled and sealed along the top to form a sealed, fluid filled inner chamber 14. The components of the port assembly 12 are molded of suitable plastic materials that are attachable by a saddle flange to the outer film layer, preferably by a thermal bonding process.

Figure 12:
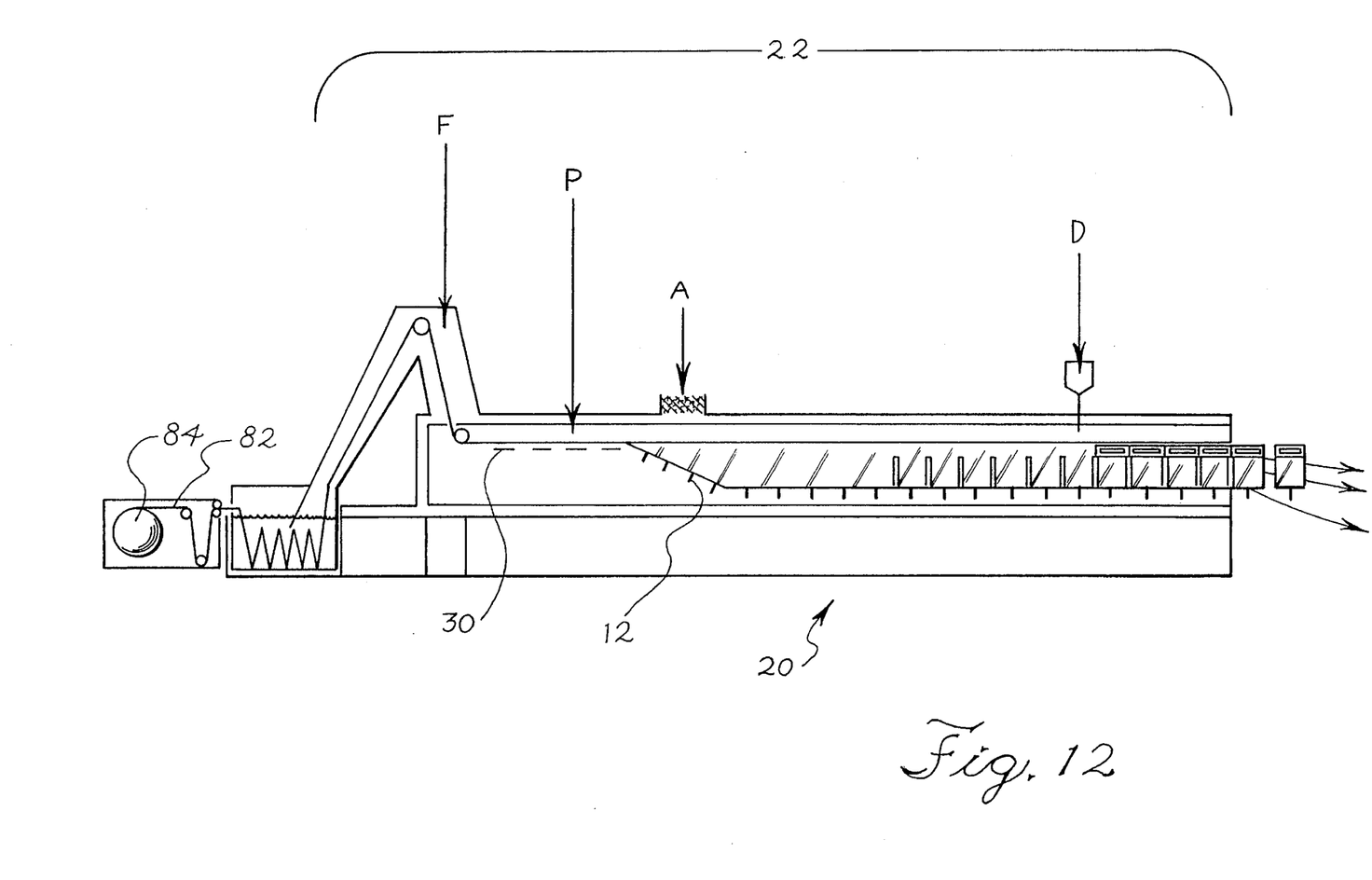
FIG. 12 is a schematic depiction of a form, fill and seal packaging machine and sterile core that might be use to assemble the flexible solution container and port assembly according to the present invention.

The flexible container 10 is preferably manufactured by a form, fill and seal packaging machine 20 as schematically depicted in FIG. 12. The forming of the flexible container, the filling with a sterile solution and the sealing of the flexible container is performed in a sterile core environment 22 associated with the packaging machine. The product solution is pre-sterilized outside of the sterile core 22. The product solution is maintained sterile as it is filled and sealed in the flexible container. The port assembly 12 is also pre-sterilized outside of the sterile core and attached to the flexible container 10 in the sterile core. The packaged end product is thus a sterile solution in a sterile container with an attached sterile port assembly that is suitable for medical use such as for parenteral fluid administration.

An example of a multiple-layer film that is suitable for form, fill and seal processing into a flexible container is as follows. A multiple layered, extrusion laminated flexible film has a bondable inside layer, a gas barrier layer, a thermal stability layer, appropriate bonding layers and a bondable outside layer.

Referring again to FIG. 12, the laminated film sheet 82 is initially horizontally flat as it longitudinally enters the form, filled and sealed packaging machine 20. A longitudinal middle line, hereafter referred to as the "saddle" line longitudinally divides the film sheet into substantially equal and mirror-image first and second sidewall portions.

A plurality of discrete, outward (i.e. downward) extending fluid sumps 30 are formed generally along the saddle line, such that the longitude axis of each sump is along or coincident with the saddle line. The sump is preferably created by a thermo-forming process. A discrete relevant portion of the film 82 is heated and permanently stretched outward to form the sump 30. The sump preferably has a smooth interior radius, as for example a generally ellipsoidal shape. The sump can be formed by permanently stretching the film beyond recovery by applying heat and a forming mandrel from the inside layer of the film. Alternatively, the sump can be formed by applying heat and drawing a vacuum from the outside surface, or a combination of these or other known thermo-forming processes.

The first and second sidewall portions of the film sheet are then inwardly folded over the saddle line so as to form a U-shaped trough. The bottom surface 40 of the trough includes the stretched fluid sump 30. The saddle flange 56 of the port member 12 is attached, preferably by a thermo-bonding or fusing process to the outside bondable surface layer of the laminated film at the sump 30.

Figures 1, 2:
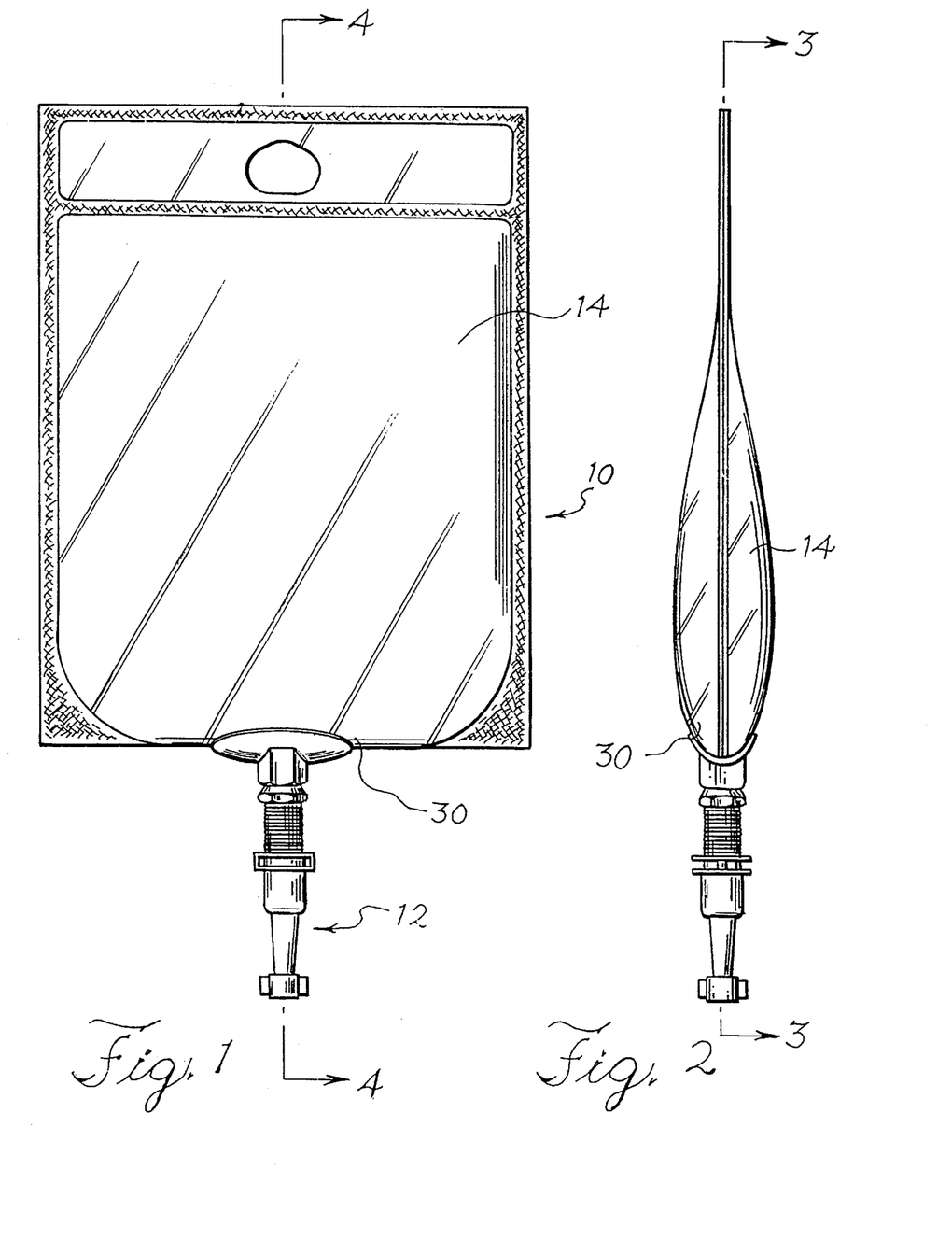
FIG. 1 is an elevation view of a filled and ready to use flexible solution container and the attached port assembly according to the present invention.
FIG. 2 is a side view of the filled flexible solution container and the attached port assembly of FIG. 1.
Figures 3, 4:
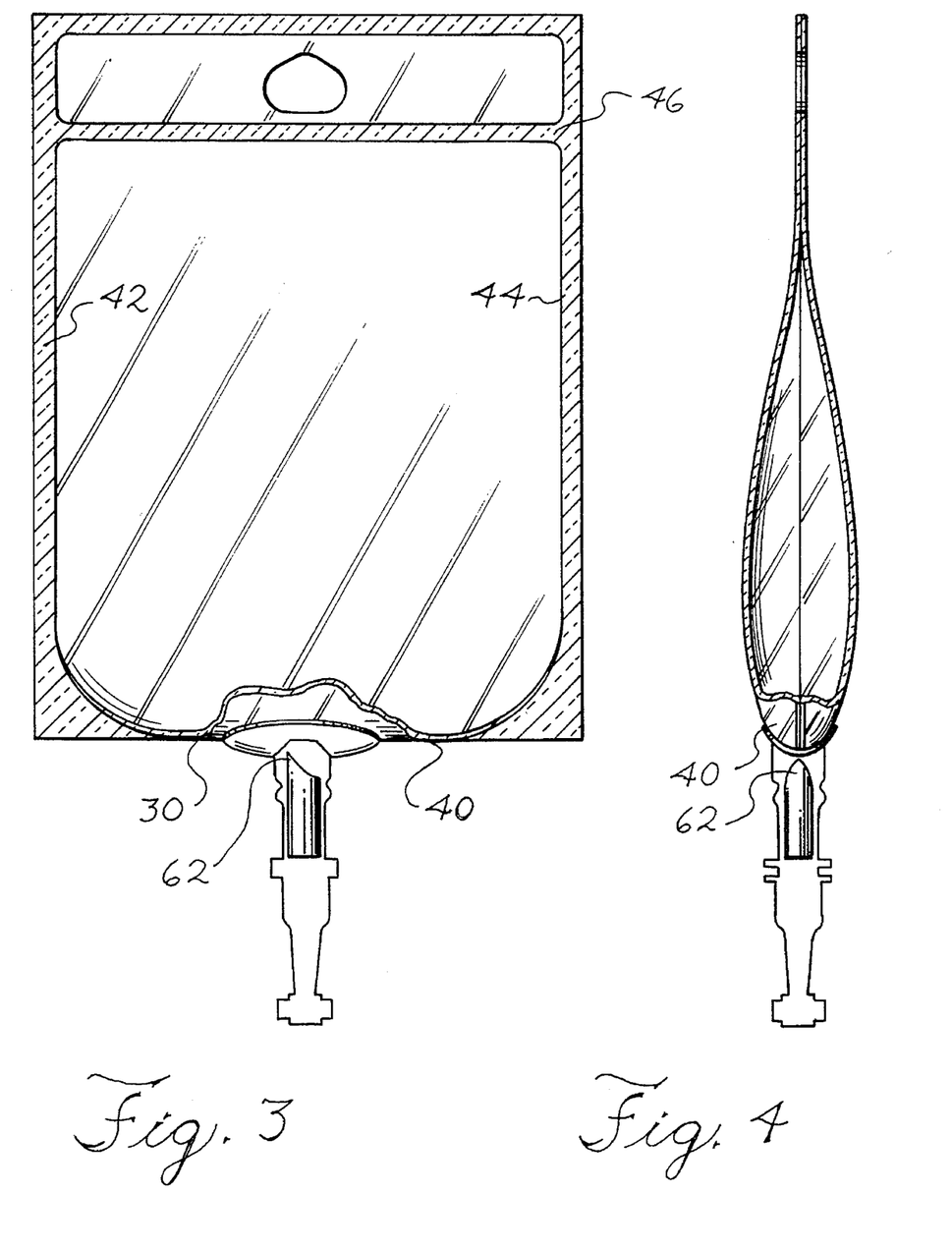
FIG. 3 is an elevation cross section view of the preferred embodiment of the flexible solution container and attached port assembly according to the present invention.
FIG. 4 is a side cross section view of FIG. 3.

Referring now to FIG. 3 the inner layer of the opposed first and second laminated film sidewall portions are sealed together along a first sealing line extending from and generally perpendicular to the bottom surface 40 so as to form a first transverse side seal 42. The inner layer is also sealed together along a second sealing line parallel to the first line, but an equal distant on the other side of the fluid sump 30 so as to form a second transverse side seal 44. Together the first side seal 42, the bottom surface 40 and the second side seal 44 form an open pouch.

The open pouch is formed within the sterile core 22 and is contacted only by the sterile filtered air of the sterile core. Next, the pouch may be optionally flushed with a flushing agent if it is to be filled with an oxygen or other air component sensitive drug. After the pouch is flushed as needed and filled with the sterile solution, the top portion of the pouch is sealed together along a third sealing line 46 so as to form a hermetically sealed, fluid filled inner chamber 14 between the first and second laminated film portions.

Referring now to FIGS. 5–8, the port assembly 12 includes a tubular member 50, a cylindrical penetrator element 60, and a cover member 80. The tubular port member 50 has a first 52 and second 54 open end and is molded preferably of a heat bondable medical grade plastic. Preferably the port member is a similar bondable (i.e. compatible) if not the same material as the inner layer of the laminated film. For example, the tubular port member 50 is preferably injection molded from an olefin. The tubular port member includes an integral and circumferential saddle flange 56 that surrounds the first open end 52 of the tubular port. The flange is preferably ellipsoid in shape and has a contoured flange face 57 of the same longitudinal and latitudinal shape as the outward stretched fluid sump portion 30 of the flexible bag. The substantially ellipsoidal shape of the contoured flange is circumferentially sealed around the orifice of the first open end 52 of the tubular port so that there is an annular (i.e. circumferential) fluid seal around the diaphragm portion 55 between the inner surface of the flange 56 and the outer surface layer of the film at the fluid sump 30.

Figure 5:
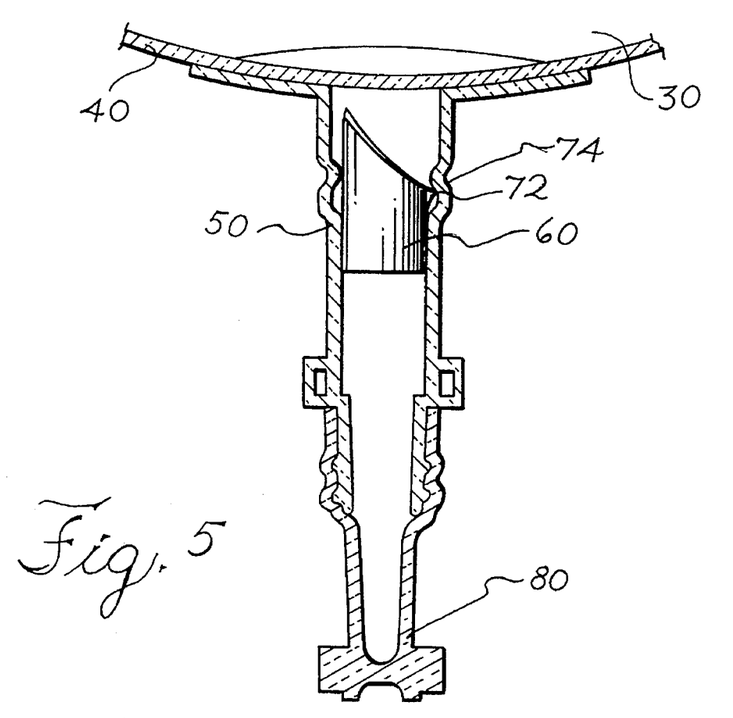
FIG. 5 is a partial cross section of the assembled port system according to the present invention.
Figure 6:
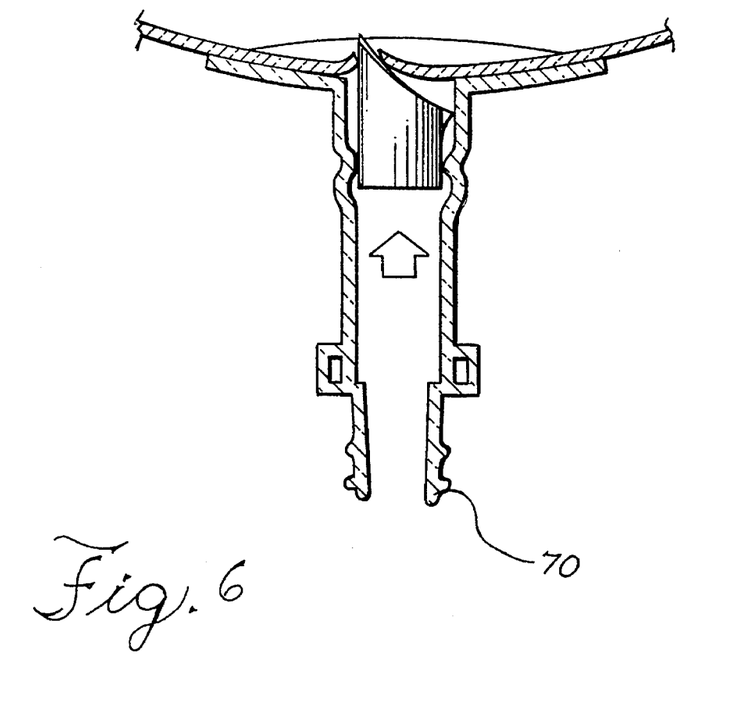
FIG. 6 is a partial cross section similar to FIG. 5 showing the penetrator element of the port system in the activated condition and in position for fluid flow.
Figure 7A:
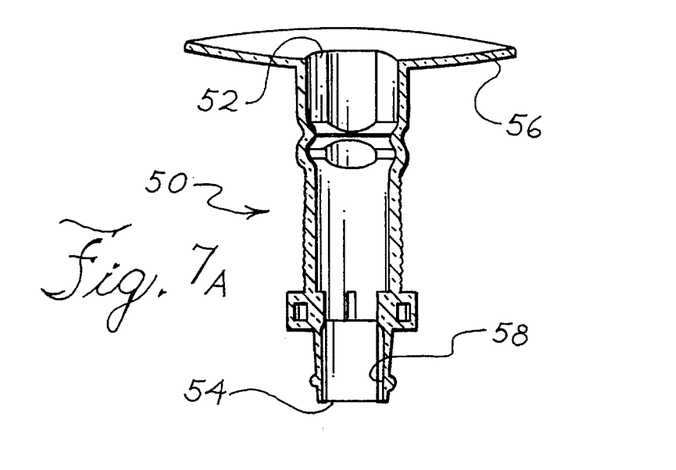
FIG. 7A is a cross section view of the tubular port member according to the present invention.
Figure 7B:
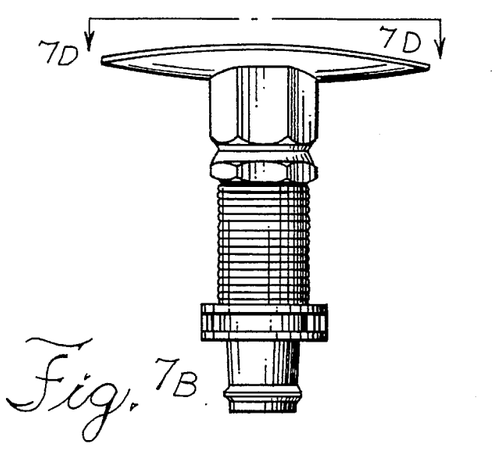
FIG. 7B is an elevation view of the port member of FIG. 7A.
Figure 7C:
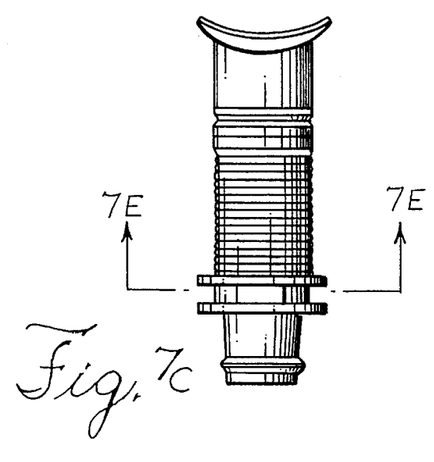
FIG. 7C is a side view of FIG. 7B.
Figure 7D:
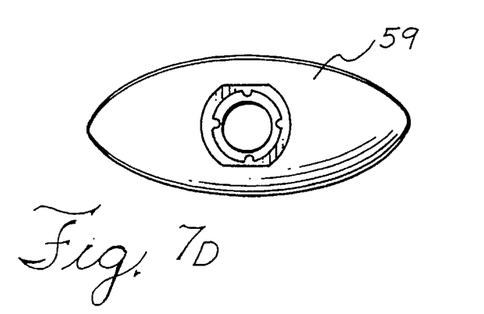
FIG. 7D is an end view along line D—D of FIG. 7B.
Figure 7E:
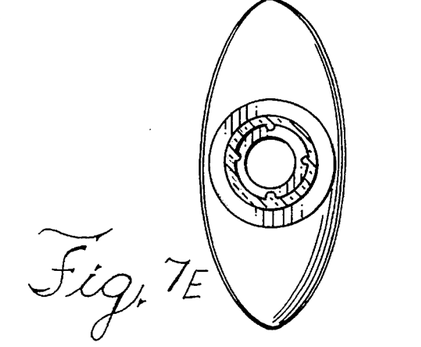
FIG. 7E is a sectional view along line E—E of FIG. 7C.

The second opened end 54 of the tubular port is provided with an administrative or access fitment 58 that fluid tight when connected with convention medical fluid connectors such as piercing pins. A removable cover 80, preferably made of an injection molded material or a compression set resilient elastomer material, is provided for closing and maintaining the sterility of the fitment 58 at the second open end 54 of the tubular port.

Since the pierceable diaphragm of the port assembly 12 according to the present invention is the laminated film material of the flexible container itself, a mechanism to pierce the film sheet and penetrate the fluid filled inner chamber 14 must be provided. In previously described flexible containers, the diaphragm element is located near the second open end (i.e. near 54) of the port system. However, in the port system of the present invention, the diaphragm portion 55 is located at the first open end 52 of the port system. Even though there is an ISO standard, there are various dimensional variations among known piercing pins. Thus a dedicated piercing mechanism or penetrator 60, which functions as a universal piercing pin adapter for most of the known pins, is specifically provided for in the port system 12 of the present invention.

The cylindrical penetrator element 60 is slidably contained within the tubular port 50. The penetrator element 60 is preferably molded of a material such as polycarbonate material for example, and has a sharp, beveled end 62 for sliding movement relative to the circumferential flange 56 so as to pierce the film sheet and penetrate the sealed inner chamber 14 of the bag. The sharp end of the penetrator element has a hollow chamber 64 forwardly opening onto the face of the beveled end 62. At least one and preferably two fluid passageways are formed through the penetrator element from the sharp, beveled end for fluid communication with the penetrator hollow chamber 64. The primary passageway is a center throughbore 66 from the hollow chamber 64 at the first open end 52 to the opposite (second) open 54 end of the penetrator. The secondary passageway is a substantially longitudinally extended channel 68 along the outer cylindrical surface of the penetrator and connected radially to the hollow chamber 64 by the radial connection passageway 69. Thus the primary and secondary passageways provide fluid communication from the hollow chamber 64 of the penetrator 60 to the access fitment 58 of the port member 50.

More specifically the tubular port member 50 as shown in FIGS. 7A–7E includes a first 52 and second 54 open end. The port includes an integral circumferential saddle flange 56 surrounding the first opening 52. The flange face is preferably ellipsoid in shape and is generally complimentary with the stretched, distended surface of the fluid sump 30 of the flexible container. The port assembly also includes a slidable cylindrical penetrator 60. The cylindrical penetrator has a hollow chamber 64 in the beveled end 62 at the first open end 52 of the tubular member. Preferably the other, non-piercing end 70 of the sliding penetrator member is flat, as shown in the preferred embodiment. Alternatively, the penetrator could be symmetrical and have two beveled faces at opposite ends for ease of assembly.

Figure 8A:
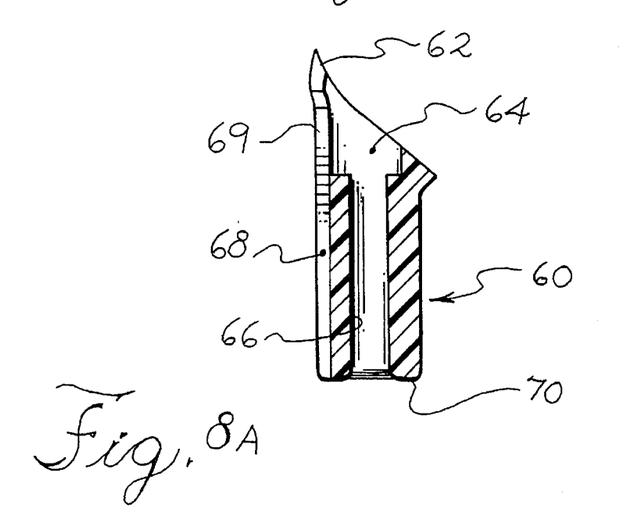
FIG. 8A is a cross section view of the penetrator element according to the present invention.
Figure 8B:
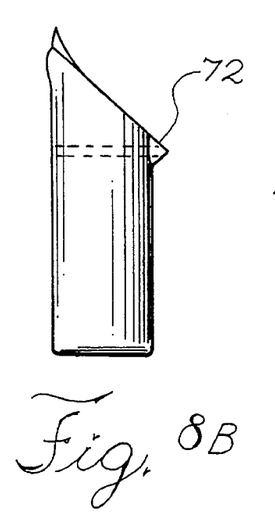
FIG. 8B is an elevation view of the penetrator element of FIG. 8A.
Figure 8C:
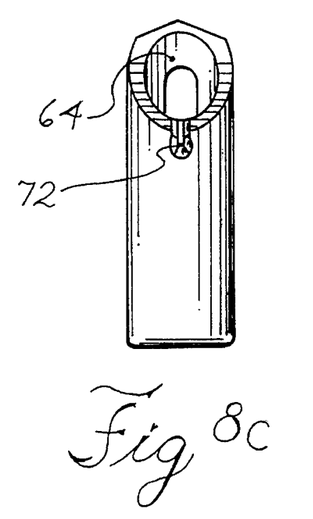
FIG. 8C is a right side view of FIG. 8B.
Figure 8D:
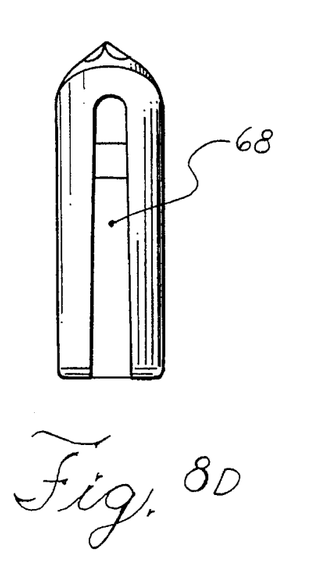
FIG. 8D is a left side view of FIG. 8B.
Figure 8E:
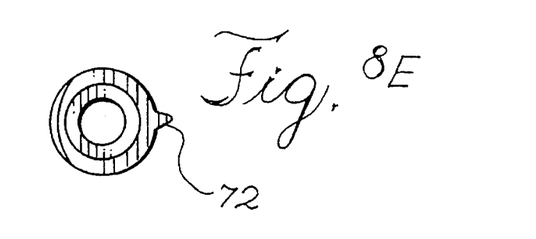
FIG. 8E is a top end view of FIG. 8B.

The penetrator 60 includes a primary fluid passage such as a center throughbore 66 from the hollow chamber in the beveled end 62 of the penetrator through the cylindrical body of the penetrator. As best seen in FIGS. 8A and 8D, the penetrator 60 further includes a secondary longitudinal channel 68 substantially along the outer cylindrical surface of the penetrator. The channel is radially connected to the hollow chamber 64 at the beveled end of the penetrator by a radial connection passage 69.

The penetrator also includes a protruding knob 72 that is initially keyed within a radial shoulder 74 on the inner surface of the tubular port member 50 for initially holding the penetrator 60 in the inactive position. The knob 72 is also preferable keyed to a longitudinal channel on the inner cylindrical surface of the port member 50 so as to prevent the penetrator from twisting as it is activated and inserted through the laminated film and into the fluid filled inner chamber 14 of the bag. Rotation of the penetrator 60 could orient the sharp end 62 of the penetrator near either of the side walls of the flexible container and thus increase the risk of an accidental pin puncture of the side wall of the flexible container. The preferred orientation of the beveled end 62 of the penetrator is shown in FIGS. 3 and 4 for example.

Figure 9A:
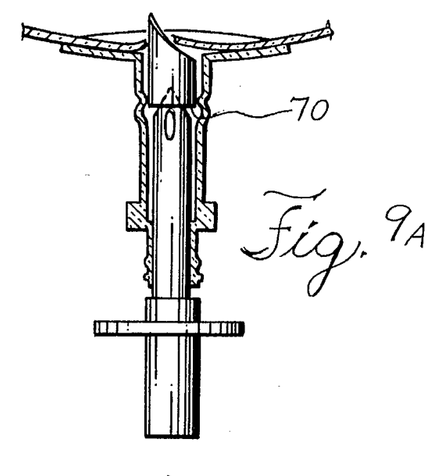
FIG. 9A is a partial cross section of the port assembly according to the present invention when activated by a center point spiking pin.
Figures 10A, 10B, 11A, 11B:
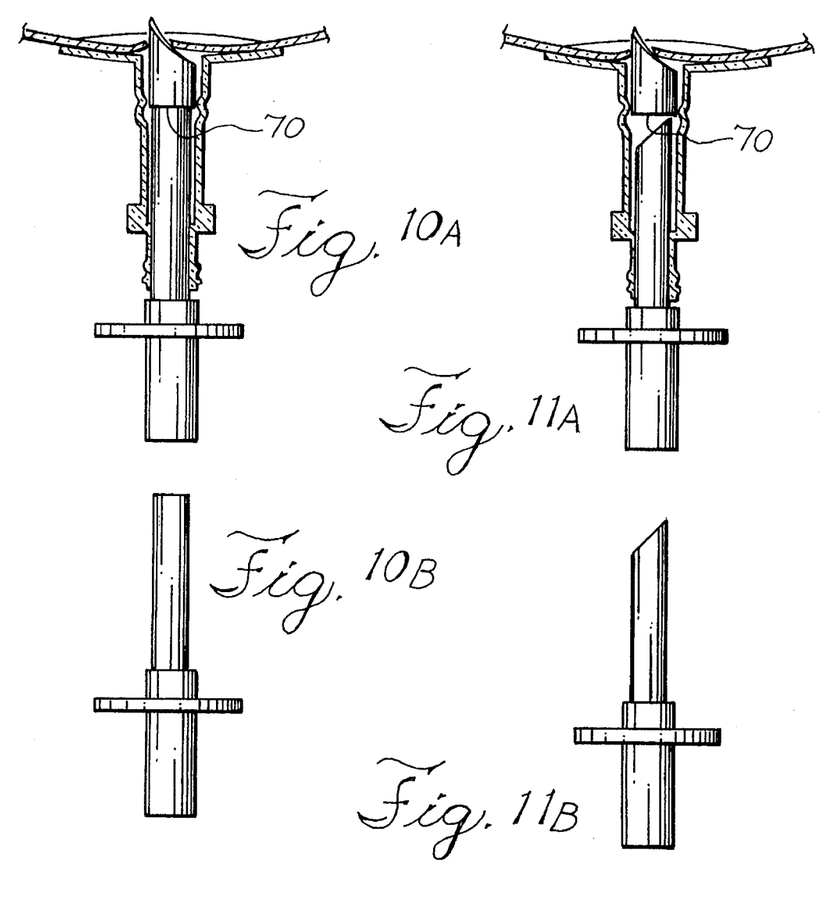
FIG. 10A is a partial cross section of the port assembly according to the present invention when activated by a blunt spiking pin.
FIG. 10B is an elevation view of a blunt spiking pin.
FIG. 11A is a partial cross section of the port assembly according to the present invention when activated by a beveled spiking pin.
FIG. 11B is an elevation view of a beveled spiking pin.

As shown in FIGS. 9A, 10A, and 11A, the second end 70 of the penetrator 60 is flat and able to adapt to any convention piercing pin configuration. Fluid flow through the penetrator is assured by either the primary center throughbore 66 or the secondary longitudinal channel 68 along the outside cylindrical edge.

The fluid sump 30 on the bottom surface of the flexible container and the flow passageways 66 and 68 in the penetrator 60 facilitates less residual solution remaining in the bottom of the flexible solution container. A greater percentage of the solution in the flexible container will be readily available for flow communication through the administration ports. The hollow chamber 64 in the beveled end 62 of the penetrator facilitates that any solution in the sump will be able to flow through either the center throughbore 66 or the longitudinal channel 68 of the penetrator to the access fitment 58 of the port member 50 and ultimately to the administration set and patient. Thus the fluid sump 30 of the flexible container and the penetrator 60 of the administration port member 50 according to the present invention facilitates more complete drainage of the medical solution from the present flexible container than the other currently known and used flexible containers.

Figure 9B:
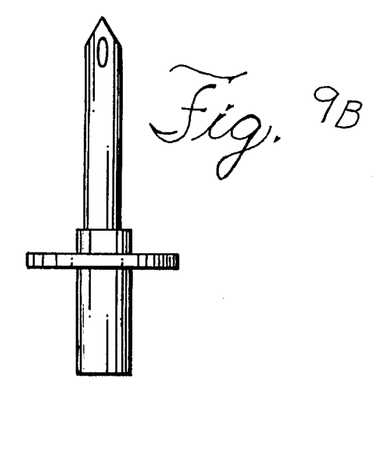
FIG. 9B is an elevation view of a center point spiking pin.
Figure 13:
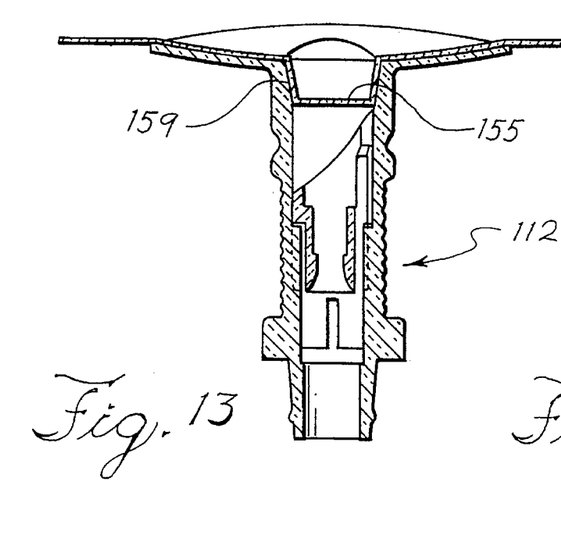
FIG. 13 is a partial cross section similar to FIG. 5 of an assembled port system according to a preferred embodiment of the present invention.
Figure 14:
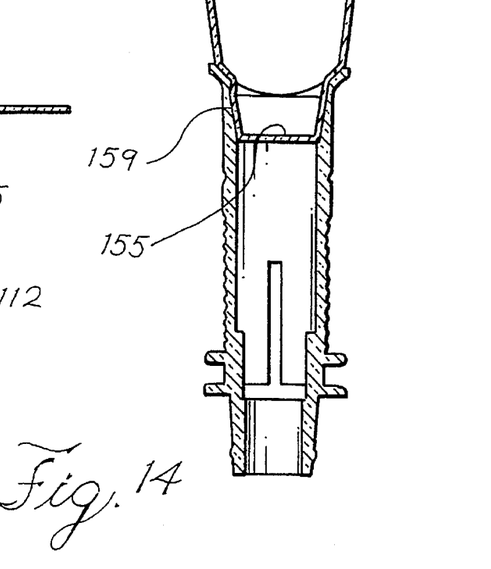
FIG. 14 is a partial cross section of FIG. 13.
Figure 15:
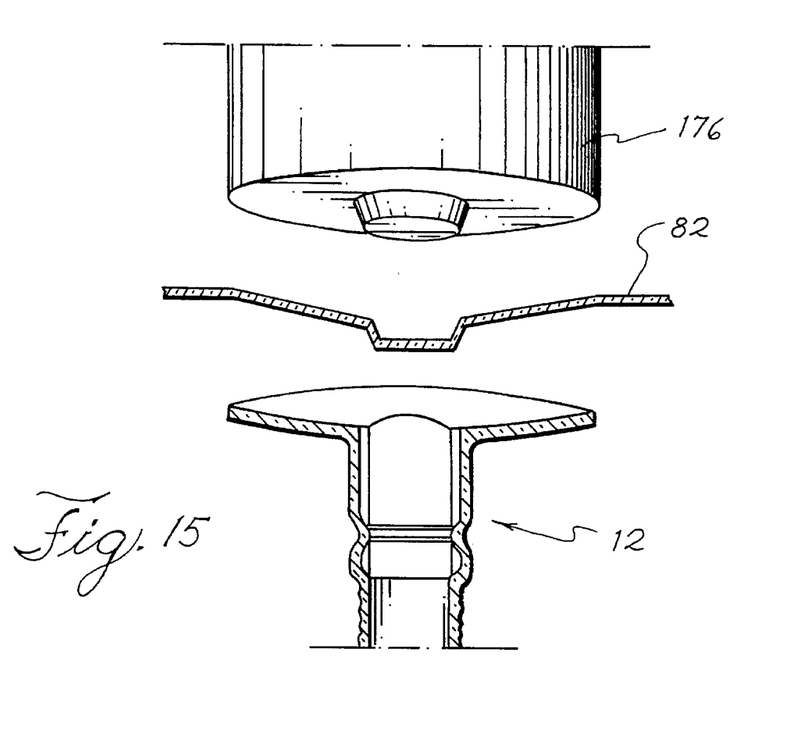
FIG. 15 is a representation of a forming mandrel used in the manufacture of the flexible container and assembled port system according to the preferred embodiment of FIG. 13.

Referring now to FIGS. 13–15, a preferred embodiment of the form, filled and sealed flexible container 10 and port assembly 12 will now be described. While the piercing pins of FIGS. 9–11 are conventional in configuration, there is a wide variety of lengths or "effective" lengths of the pin relative to the length of the penetrator 60. There are a few widely used pins whose lengths are shorter than the activation length (i.e. ISO length) the penetrator is designed to accommodate. These short pins could cause the penetrator to miss contact with the bag all together or merely stretch the bag film 40 without piercing the fluid filled inner chamber 14. Making the actual length of the penetrator 60 longer may cause the sharp, pointed end 62 of the penetrator to extend well beyond the flange and potentially damage, i.e. rupture, the sidewall of the flexible container. Also, the elastic stretch properties of the film 82 may exceed the differential shortness of a non-ISO piercing pin.

Changing the location of the diaphragm portion 155 of the film to be axially located within the port assembly 112 rather than across the first open end 52 results in more consistent performance of short piercing pins. The location of the diaphragm portion 155 of the film 82 is moved into the body of the port member 112. The location within the port allows for earlier penetration of the film by the penetrator and lessens the risk of sidewall puncture. The film is welded at predetermined angles 159 to the inside port of the member 112. Besides film protection from the sharp piercing tip, the offset diaphragm portion 155 promotes more complete drainage. The film 82 is further stretched and sealed longitudinally within port body member 50. As a result, the tip of the penetrator 60 does not slide or travel as far, if at all, into the primary bag in order to penetrate the diaphragm portion of the film. The offset location of the film in the body of the port results in a controllable weakening of the film, allowing earlier penetration of the diaphragm portion of the film and thus accommodating a wide variety of piercing pin lengths.

FIG. 15 shows a mandrel 176 that thermo-forms the film 82 within the port member 12. When the film is formed deep within the port, the port assembly can tolerate pins of shorter length. The film material 82 stretches to conform to the die without rupturing.

A sterile formed, filled and sealed packaging method will now be described with reference to FIG. 12. A continuous, longitudinal strip of multiple layer film 82 is provided in rolls 84. The film is unwound and sterilized according to a predetermined, continuous indexing movement.

The sterilized film 82 is continuously indexed and longitudinally moved (F) through the sterile core 22 of the packaging line. With the film in a horizontal orientation a uniformally and outwardly stretched plurality of fluid sump 30 are formed along the saddle line or center portion of continuous film strip. One method of forming of the sumps 30 is to apply heat to the film and use the outward movement of a forming mandrel. An alternative method for uniformally and outwardly stretching discrete center portions of the film strip to form sump portions 30 is to apply heat and a vacuum from the outside or bottom edge of the film strip.

Once the film strip has been permanently stretched to form fluid sump portions 30 along the saddle line of the film, a tubular port assembly 12 having a circumferential saddle flange 56 at one end is attached (P) to the outside surface layer of the preformed sump portion 30, preferably by thermal bonding. The inner face 57 of the saddle flange 56 is generally compatible with the outwardly stretched configuration of the fluid sump 30 to provide annular circumferential sealing around the orifice of the open end 52 of the tubular port member. Preferably the relevant portion of the film at the sump 30 is heated and the flange 56 of the port member 50 is heated and a circumferential bond seal is created around the saddle flange member 56 by application of a thermal bonding process. Alternatively, other bonding processes such as heat and pressure, ultrasonic welding, or even adhesive bonding could be used.

With the port assembly 12 now firmly bonded to the outer face of the laminated film, the wings of the flat film sheet are formed or plowed into a continuous U-shaped trough so as to define the side walls of the container. The bottom surface 40 includes the container and sump 30 and the circumferentially sealed saddle flange 56 and the two opposed portions of the inner surface layer of the multiple layer film define the side walls.

A first portion of the opposed inside layers of the film strip are formed together in a first transverse side seal 42 that extends from the bottom surface 40 to the outer edge of the film strip. The transverse side seal is generally perpendicular to the bottom surface. As the continuously indexing advances the film through the packaging machine 20, a second portion of the opposed inside layer of the strip is formed together to form a second parallel transverse side seal 44 extending from the bottom surface 40 to the top edge. The first side seal 42, the bottom surface 40, and the second side seal 44 define an open pouch.

The pouch is advanced along the packaging line in the filtered sterile air of the sterile core and is optionally flushed (A) with a flushing agent, such as $N_2$ to remove all the air from the pouch pocket as needed. A sterile solution is then metered through a filling nozzle (D) into the pouch and displaces the flushing agent or sterile air as provided.

When the pouch is filled with the metered sterile solution, a third portion along the top of the folded film strip is sealed together to form a top seal 46 and thus complete the hermetically sealed flexible container containing the sterile solution. At this point in the process, the continuous strip of filled flexible containers can exit the sterile core. Preferably the film strips are cut coincident with (i.e. in the middle of) adjacent first and second side seals 42 and 44 so as to divide the continuously formed, filled and sealed film strips into individual sealed containers. Although this cutting step may be performed inside the sterile core 22, it is preferable to perform cutting outside the core 22 since scrap or particulate will not accumulate in the sterile core.

Thus an individually sealed sterile container 10 having a sterile port assembly 12 and containing a sterile fluid in a sterile inner chamber 14 is produced. Since all of the individual components, namely the film 82, the port assembly 12, and the sterile solution have been separately sterilized and are brought together in the sterile core 22, there is no need for further sterilization such as terminal sterilization. This allows heat sensitive drugs, for example, to be pre-sterilized and package in flexible containers without degradation of the solution due to overheating during a traditional terminal sterilization process such as autoclaving.

Since the diaphragm of the port assembly 12 is the laminated flexible film 82, there is no different lower permeability in the attached port system 12 such as encountered in the previously known and described flexible containers with ports. Thus there is no need for an overwrap material for the flexible container and port assembly of the present invention, nor is there a need for a terminal sterilization process. This invention thus allows new and previously sensitive drugs and other medical solutions to be package in form, fill and sealed flexible containers.

While several embodiments of the invention have been described, modifications within the scope of the present invention may be readily apparent to one of ordinary skill in the art. All such modifications are intended to be covered by the scope of the accompanying claims.

We claim:

1. A port assembly for use with a flexible, multiple-layer film container having a laminated outer surface and a hermetically sealed inner chamber, the port assembly comprising:

a tubular body having a first and a second open end;

a integral circumferential flange surrounding the first open end of the tubular body and having a flange face circumferentially sealable to the outer surface of the container;

a fluid flow fitment at the second open end of the tubular body;

a removable cover attachable to the fluid flow fitment for closing the second open end of the tubular body; and a cylindrical penetrator slidably contained within the tubular body and having a hollow beveled end for slidably movement relative to the circumferential flange so as to pierce the surface of the flexible container and penetrate the hermetically sealed inner chamber of the flexible container and at least one passageway through the penetrator for fluid communication from the penetrated inner chamber of the flexible container to the fluid flow fitment.

2. The port assembly of claim 1 wherein the at least one passageway includes a center through bore from the hollow beveled end through the cylindrical penetrator.

3. The port assembly of claim 2 wherein the at least one passageway includes a longitudinal channel on the surface of the cylindrical penetrator and a radial connection with the hollow beveled end of the penetrator.

4. A sterile formed, filled and sealed flexible container for a sterile fluid, the container comprising:

a flexible film sheet having at least an inner film layer and an outer film layer;

a longitudinally extending saddle line dividing the film sheet into substantially equal first and second portions;

a fluid sump portion stretched outwardly from the film sheet and having a longitudinal axis along the saddle line;

the first portion of the film sheet folded over the saddle line so that the inner layer of the first portion of the film sheet opposes the inner layer of the second portion of the film sheet;

a continuous peripheral seal between the inner layer of the opposed first and second portions of the film sheet so as to form a hermetically sealed inner chamber between the first and second portions of the film sheet;

a tubular port having a first and second open end;

an integral circumferential flange surrounding the first open end of the tubular port, the flange having a contoured face circumferentially sealed to the outer layer of the film sheet along the fluid sump portion;

an access fitment at the second open end of the tubular port;

a removable cover for closing the second open end of the tubular port;

a penetrator element slidably contained within the tubular port and having a sharp end for slidable movement relative to the circumferential flange so as to pierce the film sheet and penetrate the sealed inner chamber; and at least one passageway through the penetrator element from the sharp end for fluid communication from the penetrated inner chamber to the access fitment.

5. The flexible container of claim 4 wherein the at least one passageway includes a center through bore from the sharp end.

6. The flexible container of claim 5 wherein the at least one passageway includes a substantially longitudinally extending channel along the cylindrical surface of the penetrator and connected to the center through bore.

7. The flexible container of claim 4 wherein the inner and outer film layer of the flexible film sheet are fusion bondable to each other and the continuous peripheral seal is a fusion seal.

8. The flexible container of claim 4 wherein the contoured face of the circumferential flange is an ellipsoid and the fluid sump portion is generally complementary in shape to the contoured face.

9. A port assembly for use with a flexible solution container, the flexible container having a hermetically sealed inner chamber and an exposed outer surface formed from a multiple-layer, flexible film, the port assembly comprising:

a tubular member having a first and second open end;

means for attaching the first open end of the tubular member to the outer surface of the flexible container, wherein the attaching means is an integral circumferential saddle flange at the first open end;

means for fluid flow connection at the second open end of the tubular member, wherein the connection means is a fluid connection fitment at the second open end;

means in the tubular member for slidably puncturing the flexible film and penetrating the inner chamber; and means in the tubular member for fluid passage from the punctured inner chamber to the fluid flow connection means.

10. The port assembly of claim 9 wherein the flexible container has an extended sump portion and the saddle flange is an ellipsoid shape that is complementary in shape with the sump portion.

* * * * *